United States Patent [19]

Regel et al.

[11] Patent Number: 4,875,928
[45] Date of Patent: Oct. 24, 1989

[54] SUBSTITUTED AZOLYLCYCLOPROPYL-AZOLYLMETHYL-CARBINOL DERIVATIVES

[75] Inventors: Erik Regel, Wuppertal; Klaus Böckmann, Cologne; Karl H. Büchel, Burscheid; Klaus Lürssen, Bergisch-Gladbach; Wilhelm Brandes, Leichlingen; Jörg Konze, Cologne; Paul Reinecke, Leverkusen, all of Fed. Rep. of Germany

[73] Assignee: Bayer Aktiengesellschaft, Leverkusen, Fed. Rep. of Germany

[21] Appl. No.: 792,089

[22] Filed: Oct. 28, 1985

[30] Foreign Application Priority Data

Nov. 2, 1984 [DE] Fed. Rep. of Germany ....... 3440117

[51] Int. Cl.$^4$ .................. A01N 43/653; A01N 43/64; C07D 249/08; C07D 233/60
[52] U.S. Cl. ...................................... 71/92; 514/184; 514/188; 514/256; 514/269; 514/340; 514/341; 514/383; 514/397; 544/4; 544/229; 544/319; 544/333; 546/2; 546/14; 546/276; 546/278; 548/101; 548/110; 548/262; 548/336
[58] Field of Search ................... 71/92; 514/184, 188, 514/256, 269, 340, 341, 383, 397; 544/4, 229, 319, 333; 546/2, 14, 276, 278; 548/101, 110, 262, 336

[56] References Cited

U.S. PATENT DOCUMENTS 4,618,616 10/1986 Richardson et al. ............... 548/262

FOREIGN PATENT DOCUMENTS 0044605 1/1982 European Pat. Off. .
0120276 10/1984 European Pat. Off. .
0122056 10/1984 European Pat. Off. .
0122693 10/1984 European Pat. Off. .
0164246 12/1985 European Pat. Off. .

OTHER PUBLICATIONS

Journal of Organic Chemistry, vol. 48, 1983, pp. 5133-5134, K. Okuma et al., "Reaction of Dimethyloxosulfonium Methylide . . .".

Primary Examiner—Richard L. Raymond
Assistant Examiner—Patricia L. Morris
Attorney, Agent, or Firm—Sprung, Horn, Kramer & Woods

[57] ABSTRACT

Substituted azolylcyclopropyl-azolylmethyl-carbinol derivatives of the formula

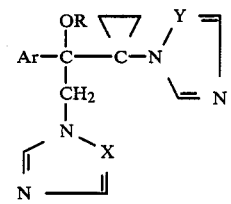

in which
  Ar is optionally substituted aryl or optionally substituted heteroaryl,
  R is hydrogen, alkyl, alkenyl, alkinyl, trialkylsilyl, optionally substituted phenylalkyl or an acyl radical, and
  X and Y each independently is a nitrogen atom or a CH group, and addition products thereof with acids and metal salts are effective in regulating plant growth and combating fungi. New intermediates are described, some of which are themselves active.

13 Claims, No Drawings

SUBSTITUTED AZOLYLCYCLOPROPYL-AZOLYLMETHYL-CARBINOL DERIVATIVES

The present invention relates to new substituted azolylcyclopropyl-azolylmethyl-carbinol derivatives, several processes for their preparation and their use as plant growth regulators and fungicides.

It has already been disclosed that certain diazolyl derivatives possess fungicidal and plant growth-regulating properties (see EP-OS (European Published Specification) 0,044,605). Thus, for example, 1,3-di-(1,2,4-triazol-1-yl)-2-(2-chlorophenyl)-propan-2-ol, 1,3-di-(1,2,4-triazol-1-yl)-2-(3-chlorophenyl)-propan-2-ol, 1,3-di-(1,2,4-triazol-1-yl)-2-(4-chlorophenyl)-propan-2-ol and 1,3-di-(1,2,4-triazol-1-yl)-2-phenyl-propan-2-ol can be used for combating fungi and for regulating plant growth. However, the action of these substances is not always completely satisfactory, especially when low amounts and concentrations are used.

New substituted azolylcyclopropyl-azolylmethylcarbinol derivatives of the formula

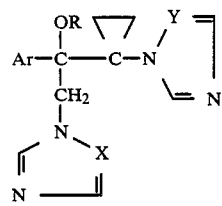

(I)

in which

Ar represents optionally substituted aryl or optionally substituted heteroaryl,

R represents hydrogen, alkyl, alkenyl, alkinyl, trialkylsilyl, optionally substituted phenylalkyl or an acyl radical, X represents a nitrogen atom or a CH group and Y represents a nitrogen atom or a CH group, and their acid addition salts and metal salt complexes have now been found.

Furthermore, it has been found that substituted azolylcyclopropyl-azolylmethyl-carbinol derivatives of the formula (I) and their acid addition salts and metal salt complexes are obtained if (a) in a first stage, aryl azolylcyclopropyl ketones of the formula

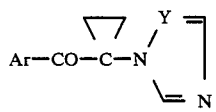

(II)

in which

Ar and Y have the meaning given above, are reacted with dimethyloxosulphonium methylide of the formula $(CH_3)_2{}^{\delta+}SO^{\delta-}CH_2$     (III)

in the presence of a diluent, and, in a second stage, the resulting aryl-azolylcyclopropyl-oxiranes of the formula

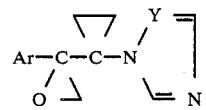

(IV)

in which

Ar and Y have the meaning given above, are reacted with azoles of the formula

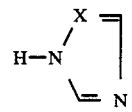

(V)

in which

X has the meaning given above, in the presence of a diluent and in the presence of a base; or (b) di-azolyl-keto-derivatives of the formula

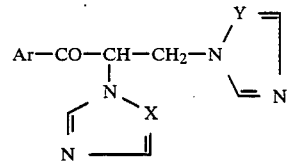

(VI)

in which

Ar, X and Y have the meaning given above, are reacted with dimethyloxosulphonium methylide of the formula $(CH_3)_2{}^{\delta+}SO^{\delta-}CH_2$     (III)

in the presence of a diluent, or (c) hydroxy compounds of the formula

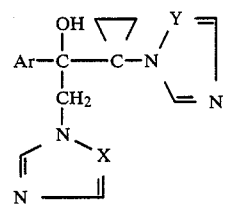

(Ia)

in which

Ar, X and Y have the meaning given above, are reacted with bases in the presence of a diluent, and the resulting alcoholates of the formula

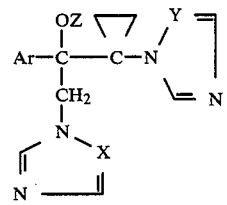

(Ib)

in which

Ar, X and Y have the meaning given above and

Z represents a base radical, are reacted with halogen compounds of the formula

R¹-Hal      (VII)

in which

R¹ represents alkyl, alkenyl, alkinyl, trialkylsilyl, optionally substituted phenylalkyl or an acyl radial and Hal represents halogen, in the presence of a diluent; and, if appropriate, the resulting compounds of the formula (I) are subjected to an addition reaction with an acid or a metal salt.

Finally, it has been found that the new substituted azolylcyclopropyl-azolylmethyl-carbinol derivatives of the formula (I) and their acid addition salts and metal salt complexes possess powerful plant growth-regulation and fungicidal properties.

Surprisingly, the substances according to the invention exhibit better plant growth-regulating and fungicidal activity than the constitutionally similar di-azolyl derivatives 1,3-di-(1,2,4-triazol-1-yl)-2-(2-chlorophenyl)-propan-2-ol, 1,3-di-(1,2,4-triazol-1-yl)-2-(3-chloro-phenyl)-propan-2-ol, 1,3-di-(1,2,4-triazol-1-yl)-2-(4-chloro-phenyl)-propan-2-ol and 1,3-di-(1,2,4-triazol-1-yl)-2-phenyl-propan-2-ol, which are known from the prior art.

Formula (I) gives a general definition of the substituted azolylcyclopropyl-azolylmethyl-carbinol derivatives according to the invention. In this formula, Ar preferably represents phenyl which is optionally monosubstituted or polysubstituted by identical or different substituents, the following preferably being mentioned as substituents: halogen; alkyl, alkoxy and alkylthio, each having 1 to 4 carbon atoms; halogenoalkyl, halogenoalkoxy and halogenoalkylthio, each having 1 or 2 carbon atoms and 1 to 5 identical or different halogen atoms, such as fluorine and chlorine atoms; and phenyl and phenoxy, each of which is optionally substituted by alkyl having 1 or 2 carbon atoms and/or halogen; and furthermore represents naphthyl, and a 5-membered or 6-membered heteroaromatic structure which is optionally monosubstituted or polysubstituted by identical or different substituents and contains nitrogen, oxygen and/or sulphur as heteroatoms, preferred substituents being the abovementioned phenyl substituents; R preferably represents hydrogen, straight-chain or branched alkyl having 1 to 4 carbon atoms, straight-chain or branched alkenyl and alkinyl, each having 2 to 4 carbon atoms, trialkylsilyl having 1 to 4 carbon atoms in each alkyl part, alkylcarbonyl having 1 to 4 carbon atoms in the alkyl part, and phenylalkyl which has 1 or 2 carbon atoms in the alkyl part and is optionally monosubstituted or polysubstituted by identical or different substituents, preferred substituents being the phenyl substituents already mentioned in the case of Ar;

X preferably represents nitrogen or a CH group and

Y represents nitrogen or a CH group.

Particularly preferred compounds of the formula (I) are those in which

Ar represents phenyl which is optionally monosubstituted to trisubstituted, in particular monosubstituted or disubstituted, by identical or different substituents, the following being mentioned as substituents: fluorine, chlorine, methyl, isopropyl, tert.-butyl, methoxy, methylthio, trifluoromethyl, trifluoromethoxy, trifluoromethylthio, and phenyl and phenoxy, each of which is optionally substituted by fluorine, chlorine and/or methyl; and furthermore represents naphthyl, and furyl, thienyl, pyridinyl or pyrimidinyl, each of which is optionally monosubstituted or disubstituted by identical or different substituents, suitable substituents being the abovementioned phenyl substitutents; R represents hydrogen, methyl, ethyl, n-propyl, isopropyl, n-butyl, isobutyl, allyl, propargyl, trimethylsilyl, methylcarbonyl, ethylcarbonyl, n-propyl-carbonyl, isopropylcarbonyl, n-butylcarbonyl, isobutylcarbonyl, and benzyl which is optionally monosubstituted to trisubstituted, in particular monosubstituted or disubstituted, by identical or different substituents, preferred substituents being the phenyl substituents already mentioned in the case of Ar;

X represents nitrogen or a CH group, and

Y represents nitrogen or a CH group.

Other preferred compounds according to the invention are addition products of acids and those substituted azolyl-cyclopropyl-azolylmethyl-carbinol derivatives of the formula (I) in which Ar, R, X and Y have the meanings which have already been mentioned as being preferred for these radicals.

The acids which can be used to form adducts preferably include hydrohalic acids, such as, for example, hydrochloric acid and hydrobromic acid, in particular hydrochloric acid, and phosphoric acid, nitric acid, sulphuric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and naphthaline-1,5-disulphonic acid.

Other preferred compounds according to the invention are addition products of salts of metals of main groups II to IV and of subgroups I and II and IV to VIII or the Periodic Table of Elements and those substituted azolyl-cyclopropyl-azolylmethyl-carbinol derivatives of the formula (I) in which Ar, R, X and Y have the meanings which have already been mentioned as being preferred for these radicals.

Salts of copper, zinc, manganese, magnesium, tin, iron and nickel are particularly preferred in this context. Suitable anions of these salts are those which are derived from acids which lead to physiologically tolerated addition products. Particularly preferred acids of this type in this context are the hydrohalic acids, such as, for example, hydrochloric acid and hydrobromic acid, and phosphoric acid, nitric acid and sulphuric acid.

The compounds listed in the table below may be mentioned as examples of substances according to the invention:

TABLE 1

(Ia)

$$\text{Ar}-\overset{\text{OH}}{\underset{\overset{|}{\text{CH}_2}}{\text{C}}}-\text{C}-\text{N}\diagup\overset{Y}{\diagdown}\diagdown_{N}$$

$$\underset{N}{\overset{N}{\diagup}}\diagdown_{X}$$

| Ar | X | Y |
|---|---|---|
| F—⟨phenyl⟩ | N | CH |

TABLE 1-continued
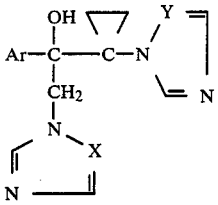 (Ia)
| Ar | X | Y |
|---|---|---|
| 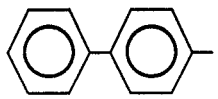 | N | CH |
| 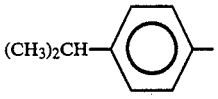 | N | CH |
| 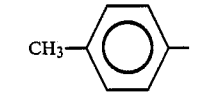 | N | CH |
| 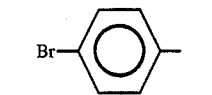 | N | CH |
| 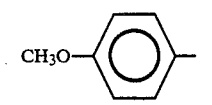 | N | CH |
| 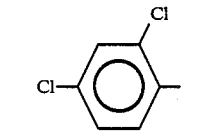 | N | CH |
| 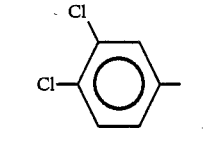 | N | CH |
| 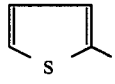 | N | CH |
| 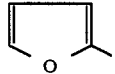 | N | CH |
| 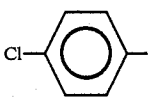 | CH | N |
| 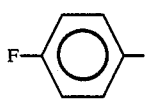 | CH | N |
TABLE 1-continued
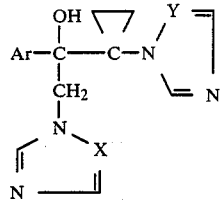 (Ia)
| Ar | X | Y |
|---|---|---|
| 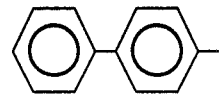 | CH | N |
| 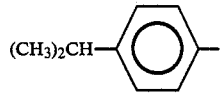 | CH | N |
| 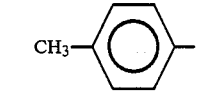 | CH | N |
| 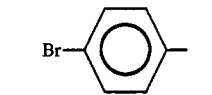 | CH | N |
| 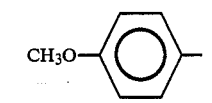 | CH | N |
| 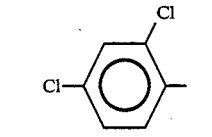 | CH | N |
| 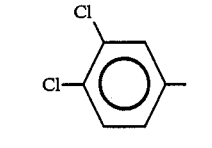 | CH | N |
| 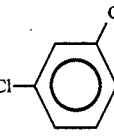 | CH | N |
| 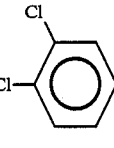 | CH | N |
| 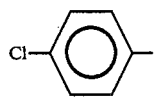 | CH | CH |
| 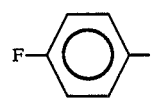 | CH | CH |

TABLE 1-continued (Ia) structure with Ar—C(OH)—C—N ring system (triazole), CH2—N ring (triazole), with substituents X and Y.

| Ar | X | Y |
|---|---|---|
| biphenyl-4-yl | CH | CH |
| 4-isopropylphenyl | CH | CH |
| 4-methylphenyl | CH | CH |
| 4-bromophenyl | CH | CH |
| 4-methoxyphenyl | CH | CH |
| 2,4-dichlorophenyl | CH | CH |
| 3,4-dichlorophenyl | CH | CH |
| thien-2-yl | CH | CH |
| furan-2-yl | CH | CH |
| thien-2-yl | N | N |
| furan-2-yl | N | N |

If, for example, 1-(4-chlorobenzoyl)-1-(1,2,4-triazol-1-yl)-cyclopropane and dimethyloxosulphonium methylide are used as starting materials, and 1,2,4-triazole is used as a reactant, the course of process (a) according to the invention can be represented by the following equation:

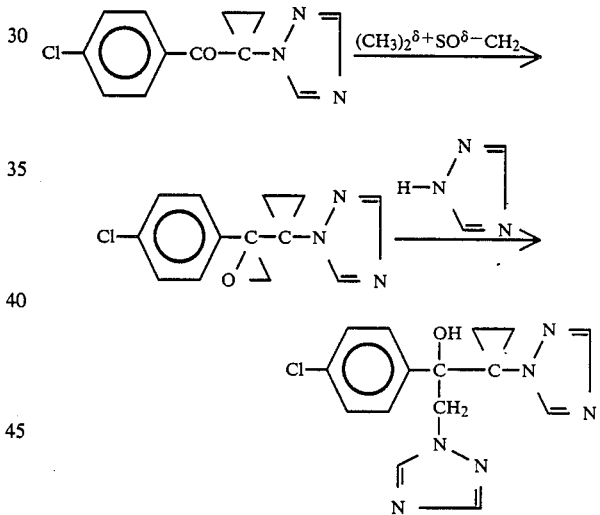

If, for example, 1-(4-chlorophenyl)-2,3-di-(1,2,4-triazol-1-yl)-propan-1-one is used as a starting material, and dimethyloxosulphonium methylide is used as a reactant, the course of process (b) according to the invention can be represented by the following equation:

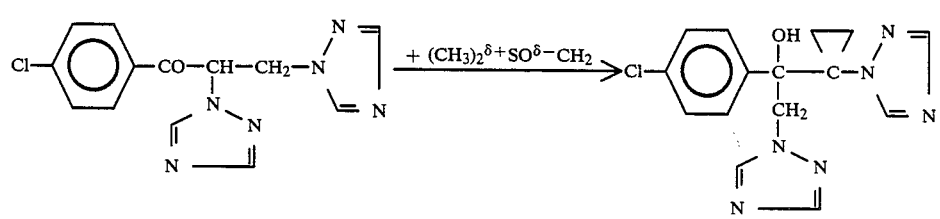

If, for example, 1-(4-chlorophenyl)-1-[1-(1,2,4-triazol-1-yl)-cyclopropyl]-2-(1,2,4-triazol-1-yl)-ethan-1-ol is used as a starting material, sodium hydride is used as the base, and iodomethane is used as a reactant, the course of process (c) according to the invention can be represented by the following equation:

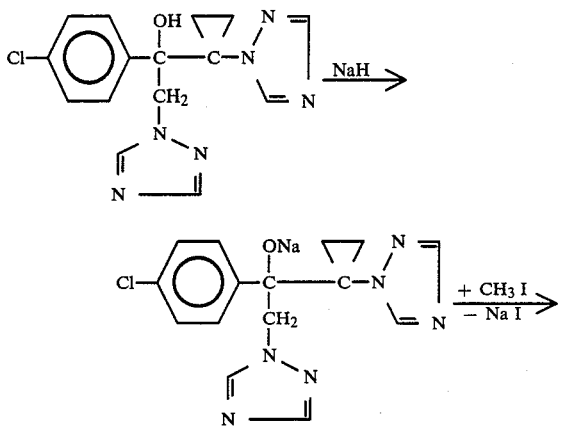

The formula (II) gives a general definition of the aryl azolylcyclopropyl ketones to be used as starting materials for process (a) according to the invention. In this formula, Ar and Y preferably have the meanings which have already been mentioned in connection with the description of the substances according to the invention, of the formula (I), as being preferred for these substituents.

The aryl azolylcyclopropyl ketones of the formula (II) are new. They are obtained by a method in which aryl halogenopropyl ketones of the formula

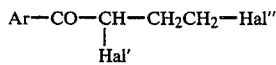 (VIII)

in which
Ar has the meaning given above and
Hal' and Hal" represent halogen, preferably bromine or chlorine,
are reacted with azoles of the formula

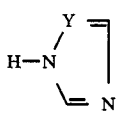 (V)

in which
Y has the meaning given above, in the presence of a diluent and in the presence of a base.

Suitable diluents for the preparation of the ketones of the formula (II) are organic solvents which are inert under the reaction conditions. These preferably include alcohols, such as, for example, ethanol, methoxyethanol or propanol; ketones, such as, for example, acetone and butan-2-one; nitriles; such as, for example, acetonitrile; esters, such as, for example, ethyl acetate; ethers, such as, for example, dioxane; aromatic hydrocarbons, such as, for example, benzene and toluene; and amides, such as, for example, dimethylformamide.

Suitable bases for this reaction are all inorganic or organic bases which can usually be employed. These preferably include alkali metal carbonates, such as, for example, sodium carbonate and potassium carbonate; alkali metal hydroxides, such as, for example, sodium hydroxide; alkali metal alcoholates, such as, for example, sodium methylate, potassium methylate, sodium ethylate and potassium ethylate; alkali metal hydrides, such as, for example, sodium hydride; and lower tertiary alkylamines, cycloalkylamines and aralkylamines, such as, in particular, triethylamine.

In carrying out this reaction, the reaction temperatures can be varied within a relatively wide range. In general, the reaction is carried out at temperatures between 0° C. and 200° C., preferably between 60° C. and 150° C.

In carrying out this reaction, 1 to 2 mols of the azole of the formula (V) and, if appropriate, 1 to 2 mols of a base are preferably employed per mol of the aryl halogenopropyl ketone of the formula (VIII). The intermediate products of the formula (II) are isolated in in a generally customary manner.

The aryl halogenopropyl ketones of the formula (VIII) are known, or can be prepared in a simple manner by customary methods (see DE-OS (German Published Specification) 2,521,104, DE-OS (German Published Specification) 2,320,355 and DE-OS (German Published Specification) 2,351,948).

The new aryl azolylcyclopropyl ketones of the formula (II) are not only suitable as starting materials for process (a) according to the invention, but constitute intermediate products of general interest.

The dimethyloxosulphonium methylide of the formula (III) which is required as a reactant both in process (a) according to the invention and in process (b) according to the invention is known (see J. Am. Chem. Soc. 87, 1363-1364 (1965)). In the above reactions, it is used in the freshly prepared state by producing it in situ by reacting trimethyloxosulphonium iodide with sodium hydride or sodium amide, in particular with potassium tert.-butylate or sodium methylate, in the presence of a diluent.

The aryl-azolylcyclopropyl-oxiranes of the formula (IV) which occur as intermediate products in process (a) according to the invention were hitherto unknown. They constitute intermediate products of general interest.

The azoles of the formula (V) which are furthermore required as starting materials for the second stage of process (a) according to the invention are generally known compounds of organic chemistry.

Formula (VI) gives a general definition of the di-azolyl-keto derivatives to be used as starting materials for process (b) according to the invention. In this formula, Ar, X and Y preferably have the meanings which have already been mentioned in connection with the description of the substances according to the invention, of the formula (I), as being preferred for these substituents.

The di-azolyl-keto derivatives of the formula (VI) are new. They are obtained by reacting aryl azolylmethyl ketones of the formula

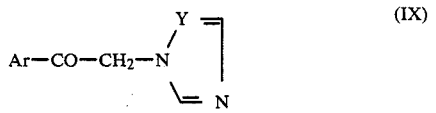 (IX)

in which
Ar and Y have the above meaning, with hydroxymethylazoles of the formula

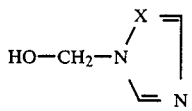

(X)

in which

X has the above meaning, in the presence of a catalyst and in the presence of a diluent.

Preferred diluents for this process for the preparation of the di-azolyl-keto derivatives of the formula (VI) are inert organic solvents. These preferably include alcohols, such as methanol and ethanol; ethers, such as tetrahydrofuran and dioxane; aromatic hydrocarbons, such as benzene and toluene; and halogenated aliphatic and aromatic hydrocarbons, such as methylene chloride, chloroform, chlorobenzene and dichlorobenzene.

This process is carried out in the presence of a catalyst. All customarily usable acidic and, in particular, basic catalysts and their buffer mixtures can be employed. These preferably include Lewis acids, such as, for example, boron trifluoride, boron trichloride, tin tetrachloride or titanium tetrachloride; organic bases, such as pyridine and piperidine; and in particular piperidine acetate.

In carrying out this process, the reaction temperatures can be varied within a relatively wide range. In general, the reaction is carried out at between 20 and 160° C., preferably at the boiling point of the particular solvent.

In carrying out this process, 1 to 1.5 mols of the hydroxymethylazole of the formula (X) and catalytic to 0.2 molar amounts of catalyst are employed per mol of the ketone of the formula (IX).

The aryl azolylmethyl ketones of the formula (IX) are known (see, for example DE-OS (German Published Specification) 2,431,407, 2,610,022 and 2,638,470).

The hydroxymethylazoles of the formula (X) are likewise known (see EP 0 006 102 and Chem. Heterocycl. Comp. 1980, 189).

The di-azolyl-keton derivatives of the formula (VI) constitute interesting intermediate products and, when used in appropriate amounts or concentrations, also exhibit fungicidal and plant growth-regulating properties.

The hydroxy compounds of the formula (Ia) to be used as starting materials for process (c) according to the invention are compounds according to the invention. They are converted to alcoholates of the formula (Ib) with the aid of strong bases. Compounds which are preferably used are alcohol metal amides, such as sodium amide and potassium amide, alkali metal hydrides, such as sodium hydride, quaternary ammonium hydroxides and phosphonium hydroxides. In the compounds of the formula (Ib), Z therefore preferably represents sodium, potassium, quaternary ammonium or phosphonium.

Suitable diluents for the conversion of the compounds of the formula (Ia) to the alcoholates of the formula (Ib) are inert organic solvents. Ethers, such as dioxane, are preferably used.

The conversion of the compounds of the formula (Ia) to the alcoholates of the formula (Ib) is preferably carried out at room temperature.

Formula (VII) gives a general definition of the halogen compounds required as reactants in process (c) according to the invention. In this formula, $R^1$ preferably has the meanings which have already been mentioned in connection with the description of the substances according to the invention, of the formula (I) as being preferred for the substituent R, with the exception of the meaning of hydrogen. Hal preferably represents chlorine, bromine or iodine.

The halogen compounds of the formula (VII) are generally known compounds of organic chemistry.

Suitable diluents for the first stage of process (a) according to the invention are inert organic solvents. These preferably include ethers, such as tetrahydrofuran or dioxane, aliphatic and aromatic hydrocarbons, such as, in particular, benzene, toluene or xylene; and dimethyl sulphoxide.

In carrying out the first stage of process (a) according to the invention, the reaction temperature can be varied within a relatively wide range. In general, the reaction is carried out at between 0° and 100° C., preferably between 10° and 60° C.

In carrying out the first stage of process (b) according to the invention, 1 to 3 mols of dimethyloxosulphonium methylide of the formula (III), produced in situ from trimethyloxosulphonium iodide in dimethyl sulphoxide and sodium hydride, are preferably employed per mol of the aryl azolylcyclopropyl ketone of the formula (II). The intermediate products of the formula (IV) are isolated in a generally customary manner.

Suitable diluents for the second stage of process (a) according to the invention are inert organic solvents. Solvents which are preferably used are nitriles, such as, in particular, acetonitrile; aromatic hydrocarbons, such as benzene, toluene and dichlorobenzene; formamides, such as, in particular, dimethylformamide; and hexamethylphosphoric acid triamide.

The second stage of process (a) according to the invention is carried out in the presence of a base. Suitable bases are all inorganic and organic bases which can customarily be used. These preferably include alkali metal carbonates, such as, for example, sodium carbonate and potassium carbonate; alkali metal hydroxides, such as, for example, sodium hydroxide; alkali metal alcoholates; such as, for example, sodium methylate, potassium methylate, sodium ethylate and potassium ethylate; alkali metal hydrides, such as, for example, sodium hydride; and lower tertiary alkylamines, cycloalkylamines and aralkylamines, such as, in particular, triethylamine.

In carrying out the second stage of process (a) according to the invention, the reaction temperature can be varied within a relatively wide range. In general, the reaction is carried out at temperatures between 0° C. and 200° C., preferably between 60° C. and 150° C.

In carrying out the second stage of process (a) according to the invention, 1 mol of the oxirane of the formula (IV) per 1 to 2 mols of the azole of the formula (V) and 1 to 2 mols of the base are preferably employed. The end products are isolated in a generally customary manner.

The reaction conditions for carrying out process (b) according to the invention correspond to those for carrying out the first stage of process (a).

In the reaction of alcoholates of the formula (Ib) with halogen compounds of the formula (VII) by process (c) according to the invention, suitable diluents are inert organic solvents. These preferably include ethers, such as diethyl ether or dioxane; aromatic hydrocarbons, such as benzene; in specific cases, also chlorinated hydrocarbons, such as chloroform, methylene chloride or carbon tetrachloride; and hexamethylphosphoric acid triamide.

In the reaction of alcoholates of the formula (Ib) with halogen compounds of the formula (VII) by process (c) according to the invention, the reaction temperatures can be varied within a relatively wide range. In general, the reaction is carried out at temperatures between 0° C. and 120° C., preferably between 20° C. and 100° C.

In carrying out process (c) according to the invention, 1 to 2 mols of a halogen compound of the formula (VII) are preferably employed per mol of an alcoholate of the formula (Ib). To isolate the end products, the reaction mixture is freed from the solvent, and water and an organic solvent are added to the residue. The organic phase is separated off, and worked up in a customary manner, and the product is purified.

In a preferred embodiment, process (c) is advantageously carried out as follows: a hydroxy compound of the formula (Ia) is used as a starting material, this compound, in a suitable organic solvent, is converted by means of an alkali metal hydride or alkali metal amide to an alkali metal alcoholate of the formula (Ib), and the latter is reacted directly, without isolation, with a halogen compound of the formula (VII), the compounds according to the invention, of the formula (I), being obtained in one operation, with elimination of alkali metal halides.

In a further preferred embodiment of process (c), the preparation of the alcoholates of the formula (Ib) and the alkylation with compounds of the formula (VII) are advantageously carried out in a two-phase system, such as, for example, aqueous sodium hydroxide solution or potassium hydroxide solution/toluene or methylene chloride, with the addition of 0.01–1 mol of a phase-transfer catalyst, such as, for example, an ammonium or phosphonium compound, reaction between the halogen compounds present in the organic phase and the alcoholates taking place in the organic phase or at the boundary.

The acid addition salts of the compounds of the formula (I) can be obtained in a simple manner by customary salt formation methods, for example by dissolving a compound of the formula (I) in a suitable inert solvent and adding the acid, for example hydrochloric acid, and can be isolated in a known manner, for example by filtration, and, if appropriate, purified by washing with an inert organic solvent.

The metal salt complexes of the compounds of the formula (I) can be obtained in a simple manner by customary processes, for example by dissolving the metal salt in an alcohol, for example ethanol, and adding the solution to compounds of the formula (I). Metal salt complexes can be isolated in a known manner, for example by filtration, and, if appropriate, purified by recrystallization.

The active compounds according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants of their environment and the way in which the compounds are applied. In every case, growth regulators are intended to influence the crop plants in the particular manner desired.

Plant growth regulating compounds can be employed, for example, to inhibit vegetative growth of the plants. Such inhibition of growth is inter alia of economic interest in the case of grasses, since it is thereby possible to reduce the frequency of cutting the grass in ornamental gardens, parks and sports grounds, at verges, at airports or in fruit orchards. The inhibition of growth of herbaceous and woody plants at verges and in the vicinity of pipelines or overland lines or, quite generally, in areas in which heavy additional growth of plants is undesired, is also of importance.

The use of growth regulators to inhibit the growth in length of cereals is also important. The danger of "lodging" of the plants before harvesting is thereby reduced or completely eliminated. Furthermore, growth regulators can strengthen the stem of cereals, which again counteracts lodging. Use of growth regulators for shortening and strengthening the stem enables higher amounts of fertilizer to be applied to increase the yield, without danger of the cereal lodging.

In the case of many crop plants, inhibition of the vegetative growth makes denser planting possible, so that greater yields per area of soil can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soybeans or cereals. Using growth regulators it is also possible, for example, to inhibit the degradation of desired constituents, such as, for example, sugar in sugar beet or sugar cane, before or after harvesting. It is also possible favorably to influence the production or the efflux of secondary plant constituents. The stimulation of latex flux in rubber trees may be mentioned as an example.

Parthenocarpous fruit can be formed under the influence of growth regulators. Furthermore the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is a great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the other hand, it is possible to prevent premature shedding of fruit. However, on the other hand, shedding of fruit, or even the fall of blossom, can be promoted up to a certain degree ("thinning out") in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating cereal diseases, such as mildew, rust, Septoria and Fusarium species and Pyrenophora teres; and furthermore for combating rice diseases, such as Pyricularia oryzae; and Venturia species, such as *Venturia inaequalis*. Furthermore, the substances according to the invention have a broad and good fungicidal in vitro action spectrum.

When used in appropriate amounts, the substances according to the invention also exhibit a herbicidal action.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example, ground natural minerals, such as kaolins, clays, talc, chalk, quartz, attapulgite, montmorillonite or diatomaceous earth, and ground synthetic minerals, such as highly disperse silicic acid, alumina and silicates. As solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foamforming agents there are suitable: for example, nonionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products. As dispersing agents there are suitable: for example, ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, cooper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, coating and the like. Furthermore, it is possible to apply the active compounds in accordance with the ultra-low volume process or to inject the active compound preparation or the active compound itself into the soil. It is also possible to treat the seeds of plants.

When the compounds according to the invention are employed as plant growth regulators, the amounts used can be varied within a relatively wide range. In general, 0.01 to 50 kg, preferably 0.05 to 10 kg, are used per hectare of soil surface.

When the substances according to the invention are employed as plant growth regulators, the rule is that they are applied within a preferred period of time, the exact definition of which depends on the climatic and vegetative circumstances.

When the substances according to the invention are employed as fungicides, the amount used can also be varied within a relatively wide range, depending on the method of application. Thus, in the treatment of parts of plants, the active compound concentrations in the use forms are in general between 1 and 0.0001% by weight, preferably between 0.5 and 0.001% by weight. In the treatment of seed, amounts of active compound of 0.001 to 50 g per kg of seed, preferably 0.01 to 10 g, are generally required. For the treatment of soil, active compound concentrations of 0.00001 to 0.1% by weight, preferably 0.0001 to 0.02%, are required at the place of action.

The preparation and the use of the active compounds according to the invention are illustrated by the examples below.

PREPARATION EXAMPLES

Example 1

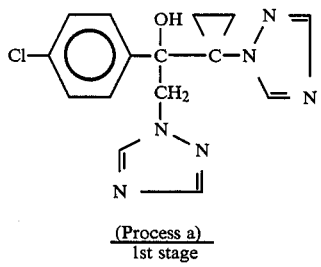

(Process a)
1st stage

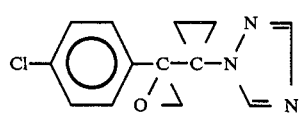

100 ml of dry dimethyl sulphoxide are added dropwise to a mixture of 3.7 g of sodium hydride (80% strength) and 26.1 of trimethylsulphoxonium iodide at 10° C., and stirring is continued for 1 hour at room temperature. Thereafter, 24 g of 1-(4-chlorobenzoyl)-1-(1,2,4-triazol-1-yl)-cyclopropane in 50 ml of dimethyl sulphoxide are added dropwise. The reaction mixture is stirred for two days at room temperature. It is then poured onto 600 ml of ice water and extracted several times with ethyl acetate, and the combined organic phases are washed with water, dried with sodium sulphate and evaporated down in vacuo. 27.2 g of 1-[1-(4-chlorophenyl)-oxiranyl]-1-(1,2,4-triazol-1-yl)-cyclopropane are obtained as a yellowish oil, which is directly reacted further (refractive index $n_D^{20}$ 1.5635).

2nd stage

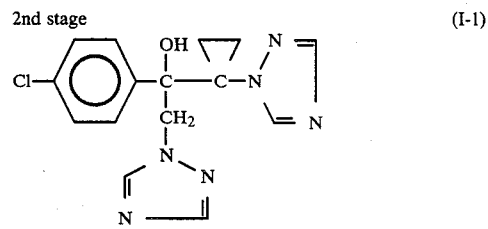

18 g of 1-[1-(4-chloropheny)-oxiranyl]-1-(1,2,4-triazol-1-yl)-cyclopropane (see 1st stage), 9.5 g of potassium carbonate and 15 g of 1,2,4-triazole in 100 ml of acetonitrile are heated under reflux for 8 hours. The reaction mixture is then evaporated down in vacuo, and the residue is taken up in a mixture of water and methylene chloride. The organic phase is separated off, washed with water, dried over sodium sulphate and evaporated down in vacuo. The residue is stirred with toluene, and the product is filtered off under suction and recrystallized from 300 ml of ethanol. 10 g (44% of theory) of 1-(4-chlorophenyl)-1-[1-(1,2,4-triazol-1-yl)-1-cyclopropyl]-2-(1,2,4-triazol-1-yl)-ethan-1-ol of melting point 211° C. are obtained.

Preparation of the starting material

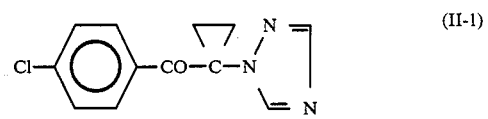

A solution of 150 g of 4-chlorophenyl 1-bromo-3-chloropropyl ketone in 200 ml of acetone is added dropwise to a boiling solution of 100 g of potassium carbonate and 110 g of 1,2,4-triazol in 400 ml of acetone, and the mixture is then stirred under reflux for 8 hours. Thereafter, it is evaporated down in vacuo, and the residue is stirred in 500 ml of water. The precipitate which separates out is filtered off under suction, washed several times with water and dried. 104 g (82% of theory) of 1-(4-chlorobenzoyl)-1-(1,2,4-triazol-1-yl)-cyclopropane of melting point 78° C. are obtained.

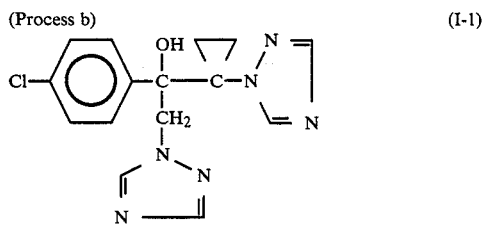

A solution of 15.1 g of 1-(4-chlorophenyl)-2,3-di-(1,2,4-triazol-1-yl)-propan-1-one in 75 ml of dimethyl sulphoxide is added dropwise to a mixture of 24.2 g of trimethylsulphoxonium iodide and 12.3 g of potassium tert.-butylate in 60 ml of dimethyl sulphoxide. The reaction mixture is stirred for 18 hours at room temperature. It is then evaporated down in vacuo. The residue is dissolved in methylene chloride, and the solution is washed with water, dried over sodium sulphate and evaporated down. The residue is purified by chromatography (silica gel/methylene chloride). The oil which remains is brought to crystallization by stirring with ether. 6.3 g (38.2% of theory) of 1-(4-chlorophenyl)-1-[1-(1,2,4-triazol-1-yl)-1-cyclopropyl]-2-(1,2,4-triazol-1-yl)ethan-1-ol of melting point 208° C. are obtained.

Preparation of the starting material

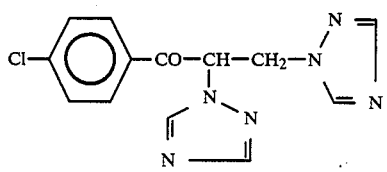
(VI-1)

A mixture of 44.3 g of 4-chlorophenyl 1,2,4-triazol-1-yl-methyl ketone, 19.6 g of 1-hydroxymethyl-1,2,4-triazole, 300 ml of toluene, 6 g of acetic acid and 2 ml of piperidine is heated under a water separator until separation of water is complete. The mixture is allowed to cool, and the crystalline precipitate formed is filtered off under suction and washed with diisopropyl ether. 47 g (76% of theory) of 1-(4-chlorophenyl)-2,3-di-(1,2,4-triazol-1-yl)-propan-1-one of melting point 240° C. are obtained.

The substances of the formula (I) which are listed in the table below can be prepared in an analogous manner by the process according to the invention.

TABLE 2

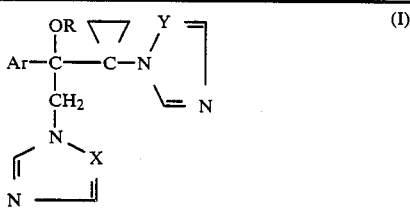
(I)

| Example No. | Ar | R | X | Y | Melting point (°C.) |
|---|---|---|---|---|---|
| I-2 | F—⬡— | H | N | N | 182 |
| I-3 | ⬡—⬡— | H | N | N | 184 |
| I-4 | (CH₃)₂CH—⬡— | H | N | N | 167 |

TABLE 2-continued (I)

| Example No. | Ar | R | X | Y | Melting point (°C.) |
|---|---|---|---|---|---|
| I-5 | CH₃—⬡— | H | N | N | 148 |
| I-6 | ⬡— | H | N | N | 146 |
| I-7 | Br—⬡— | H | N | N | 202 |
| I-8 | Cl,Cl—⬡— (2,4-diCl) | H | N | N | 166 |
| I-9 | CH₃O—⬡— | H | N | N | 178 |
| I-10 | Cl—⬡— | H | N | CH | 196 |
| I-11 | CH₃O—⬡— | H | CH | N | 213 |

The precursors of the formula (II) which are listed in the table below are obtained similarly to Example 1 and according to the stated process conditions.

TABLE 3

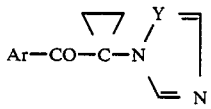
(II)

| Example No. | Ar | Y | Melting point (°C.) |
|---|---|---|---|
| II-2 | F—⬡— | N | 69 |

TABLE 3-continued $$Ar-CO-C-N\overset{Y}{\underset{N}{\diagdown}}\quad (II)$$

| Example No. | Ar | Y | Melting point (°C.) |
|---|---|---|---|
| II-3 | biphenyl-4-yl | N | 169 |
| II-4 | 4-CH₃-phenyl | N | 107 |
| II-5 | phenyl | N | 78–81 |
| II-6 | 4-Br-phenyl | N | 82 |
| II-7 | 3,4-Cl₂-phenyl | N | 84 |
| II-8 | 4-CH₃O-phenyl | N | 90 |
| II-9 | 2-methylthien-5-yl | N | 91 |

The intermediate products of the formula (IV) which are listed in the table below are obtained similarly to Example 1 and according to the stated process conditions.

TABLE 4

$$Ar-\underset{O}{\overset{\diagup}{C}}-C-N\overset{Y}{\underset{N}{\diagdown}}\quad (IV)$$

| Example No. | Ar | Y | Physical constant |
|---|---|---|---|
| IV-2 | 4-F-phenyl | N | $n_D^{20}$ 1.5412 |
| IV-3 | biphenyl-4-yl | N | oil |
| IV-4 | 4-CH₃-phenyl | N | oil |
| IV-5 | phenyl | N | oil |
| IV-6 | 4-Br-phenyl | N | oil |
| IV-7 | 3,4-Cl₂-phenyl | N | oil |
| IV-8 | 4-CH₃O-phenyl | N | oil |

The precursors of the formula (VI) which are listed in the table below are obtained similarly to Example 1 and according to the stated process conditions.

TABLE 5

$$Ar-CO-CH-CH_2-N\overset{Y}{\underset{N}{\diagdown}}\quad (VI)$$
$$\underset{N}{\overset{|}{\underset{\diagdown}{N}}}X$$

| Example No. | Ar | X | Y | Melting point (°C.) or refractive index |
|---|---|---|---|---|
| VI-2 | 4-F-phenyl | N | N | 185 |
| VI-3 | 3,4-Cl₂-phenyl | N | N | $n_D^{20}$ = 1.5504 |
| VI-4 | biphenyl-4-yl | N | N | 195 |
| VI-5 | 4-(CH₃)₂CH-phenyl | N | N | 170 |

TABLE 5-continued $$Ar-CO-CH-CH_2-N\diagup_{\diagdown N}^{Y} \quad (VI)$$
$$\underset{N}{\overset{N}{\diagdown}}\diagdown X$$

| Example No. | Ar | X | Y | Melting point (°C.) or refractive index |
|---|---|---|---|---|
| VI-6 | CH₃—C₆H₄— | N | N | 212 |
| VI-7 | C₆H₅— | N | N | 170 |

Use examples

The compounds shown below are employed as comparative substances in the use examples below:

(A) N-CH₂-C(OH)(3-Cl-C₆H₄)-CH₂-N bis(1,2,4-triazol-1-yl)

(B) N-CH₂-C(OH)(4-Cl-C₆H₄)-CH₂-N bis(1,2,4-triazol-1-yl)

(C) N-CH₂-C(OH)(C₆H₅)-CH₂-N bis(1,2,4-triazol-1-yl)

(D) N-CH₂-C(OH)(2-Cl-C₆H₄)-CH₂-N bis(1,2,4-triazol-1-yl)

(disclosed in EP-OS (European Published Specification) 0,044,605).

Example A

Inhibition of growth of rice
Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Rice is grown in a climatic chamber, in small pots containing vermiculite, until the 1st leaf reaches a size of 1-2 cm. At this stage, the pots are placed in the prepared active compound solutions up to a height corresponding to half the height of the pot.

After the development of the 3rd leaf, the length of all plants is determined and expressed as percentage of the length of the control plants. 100% denotes a growth corresponding to that of the control plants, values below 100% denote inhibition of growth, and values are 100% denote promotion of growth.

In this test, active compounds (I-1), (I-2), (I-5) and (I-7) according to the invention exhibit a powerful growth-inhibiting action.

Example B

Inhibition of growth of cotton
Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Cotton plants are grown in a greenhouse until the 5th secondary leaf has unfolded completely. In this stage, the plants are sprayed with the preparations of active compound until dripping wet. After 3 weeks, the additional growth of the plants is measured and the inhibition of growth in per cent of the additional growth of the control plants is calculated. 100% inhibition of growth means that growth has stopped and 0% denotes a growth corresponding to that of the control plants.

In this test, the active compounds (I-1), (I-2) and (I-7) according to the invention exhibit a more powerful growth-inhibiting action than the compound (A) known from the prior art.

Example C

Inhibition of growth of soya beans
Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Soya bean plants are grown in a greenhouse until the first secondary leaf has unfolded completely. In this stage, the plants are sprayed with the preparations of active compound until dripping wet. After 3 weeks, the additional growth is measured on all the plants and the inhibition of growth in per cent of the additional growth of the control plants is calculated. 100% inhibition of growth means that growth has stopped and 0% denotes a growth corresponding to that of the control plants.

In this test, the active compounds (I-1), (I-2), (I-7), (I-5) and (I-6) according to the invention exhibit a more powerful growth-inhibiting action than the compound (D) known from the prior art.

Example D

Inhibition of growth of barley
  Solvent: 30 parts by weight of dimethylformamide
  Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Barley plants are grown in a greenhouse to the 2-leaf stage. In this stage, the plants are sprayed with the preparations of active compound until dripping wet. After 3 weeks, the additional growth is measured on all plants and the inhibition of growth in per cent of the additional growth of the control plants is calculated. 100% inhibition of growth means that growth has stopped and 0% denotes a growth corresponding to that of the control plants.

In this test, the active compounds (I-2), (I-7) (I-5) and (I-6) according to the invention exhibit a more powerful growth-inhibiting action than the compounds (A), (B), (C) and (D) known from the prior art.

Example E

Stimulation of the fixation of $CO_2$ in soy beans
  Solvent: 30 parts by weight of dimethylformamide
  Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Soy bean plants are grown in a greenhouse until the first secondary leaf has unfolded completely. At this stage, the plants are sprayed with the preparations of active compound until dripping wet. In the further course of the experiment, the fixation of $CO_2$ in the plants is determined by customary methods. The values are compared with those of the control plants, which have not been treated with the active compounds. The figures of merit have the following meanings:
  − denotes inhibition of the fixation of $CO_2$
  O denotes fixation of $CO_2$ as in the case of the control
  + denotes low stimulation of the fixation of $CO_2$
  + + denotes powerful stimulation of the fixation of $CO_2$
  + + + denotes very powerful stimulation of the fixation of $CO_2$ In this test, the active compound (I-5) according to the invention shows stimulation of the fixation of $CO_2$ whereas the compounds (B) and (C), which are known from the prior art, lead to inhibition of the fixation of $CO_2$.

Example F

Venturia test (apple)/protective
  Solvent: 4.7 parts by weight of acetone
  Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaequalis) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, the compounds (I-1), (I-5) and (I-7) according to the invention exhibit a better action than the known comparative substance (C).

Example G

Pyrenophora teres test (barley)/protective
  Solvent: 100 part by weight of dimethylformamide
  Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dewmoist. After the spray coating has dried on, the plants are sprayed with a conidia suspension of Pyrenophora teres. The plants then remain in an incubation cabinet at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, the compounds (I-1) and (I-2) according to the invention exhibit a better action than the known comparative substance (B).

It will be understood that the specification and examples are illustrative but not limitative of the present invention and that other embodiments within the spirit and scope of the invention will suggest themselves to those skilled in the art.

We claim:

1. A substituted azolylcyclopropylazolylmethyl-carbinol derivative of the formula

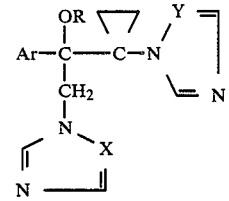

in which
  Ar is phenyl optionally substituted by halogen; alkyl, alkoxy and alkylthio, each having 1 to 4 carbon atoms; halogenoalkyl, halogenoalkoxy and halogenoalkylthio, each having 1 or 2 carbon atoms and 1 to 5 identical or different halogen atoms; and/or phenyl and phenoxy, each of which is optionally substituted by alkyl having 1 or 2 carbon atoms and/or halogen; or is naphthyl, or is furyl, thienyl, pyridinyl or pyrimidinyl, each of which is optionally substituted by the above-mentioned phenyl substituents;

R is hydrogen, alkyl having 1 to 4 carbon atoms, alkenyl or alkvinyl, each having 2 to 4 carbon atoms, trialkylsilyl having 1 to 4 carbon atoms in each alkyl part, alkylcarbonyl having 1 to 4 carbon atoms in the alkyl part, and/or phenylalkyl which has 1 or 2 carbon atoms in the alkyl part and optionally substituted by those phenyl substituents already mentioned in the case of Ar, and X and Y each independently is a nitrogen atom or a CH group, or an addition product thereof with an acid or metal salt.

2. A compound or addition product according to claim 1, in which

Ar is optionally substituted by fluorine, chlorine, methyl, isopropyl, tert.-butyl, methoxy, methylthio, trifluoromethyl, trifluoromethoxy, trifluoromethylthio, and/or phenyl or phenoxy, each of which is optionally substituted by fluorine, chlorine and/or methyl; or is naphthyl, and furyl, thienyl, pyridinyl or pyrimidinyl, each of which is optionally monosubstituted or disubstituted by the above-mentioned phenyl substitutents; and R is hydrogen, methyl, ethyl, n-propyl, isopropyl, n-butyl, isobutyl, allyl, propargyl, trimethylsilyl, methylcarbonyl, ethylcarbonyl, n-propyl-carbonyl, isopropylcarbonyl, n-butyl-carbonyl, isobutylcarbonyl, or benzyl which is optionally monosubstituted to trisubstituted by the phenyl substituents already mentioned in the case of Ar.

3. A compound according to claim 1, wherein such compound is 1-(4-chlorophenyl)-1-[1-(1,2,4-triazol-1-yl)-1-cyclo-propyl]-2-(1,2,4-triazol-1-yl)-ethan-1-ol of the formula

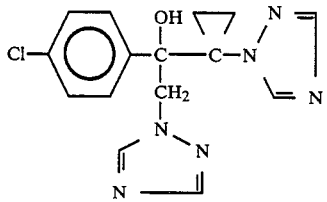

or an addition product thereof with an acid or metal salt.

4. A compound according to claim 1, wherein such compound is 1-(4-fluorophenyl)-1-[1-(1,2,4-triazol-1-yl)-1-cyclo-propyl]-2-(1,2,4-triazol-1-yl)-ethan-1-ol of the formula

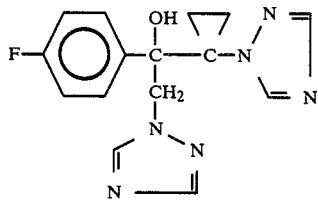

or an addition product thereof with an acid or metal salt.

5. A compound according to claim 1, wherein such compound is 1-(4-biphenyl)-1-[1,2,4-triazol-1-yl)-1-cyclo-propyl]-2-(1,2,4-triazol-1-yl)-ethan-1-ol of the formula

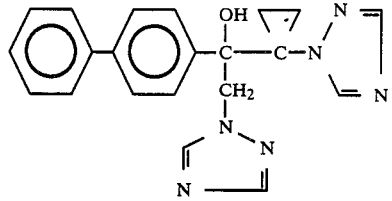

or an addition product thereof with an acid or metal salt.

6. A compound according to claim 1, wherein such compound is 1-(4-methylphenyl)-1-[1-(1,2,4-triazol-1-yl)-1-cyclo-propyl]-2-(1,2,4-triazol-1-yl)-ethan-1-ol of the formula

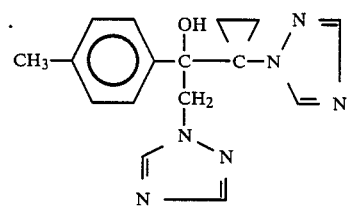

or an addition product thereof with an acid or metal salt.

7. A compound according to claim 1, wherein such compound is 1-phenyl-1-[1-(1,2,4-triazol-1-yl)-1-cyclopropyl]-2-(1,2,4-triazol-1-yl)-ethan-1-ol of the formula

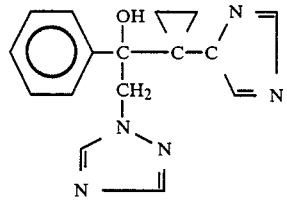

or an addition product thereof with an acid or metal salt.

8. A plant growth regulating or fungicidal composition comprising a plant growth regulating or fungicidally effective amount of a compound or addition product according to claim 1 in admixture with a diluent.

9. A method of regulating the growth of plants which comprises applying to such plants or to a locus in which such plants are growing or are to be grown a plant growth regulating effective amount of a compound or addition product according to claim 1.

10. The method according to claim 9, wherein such compound is 1-(4-chlorophenyl)-1-[1-(1,2,4-triazol-1-yl)-1-cyclopropyl]-2-(1,2,4-triazol-1-yl)-ethan-1-ol, 1-(4-fluorophenyl)-1-[1-(1,2,4-triazol-1-yl)-1-cyclopropyl]-2-(1,2,4-triazol-1-yl)-ethan-1-ol, 1-(4-biphenyl)-1-[1-(1,2,4-triazol-1-yl)-1-cyclo-propyl]-2-(1,2,4-triazol-1-yl)-ethan-1-ol, 1-(4-methylphenyl)-1-[1-(1,2,4-triazol-1-yl)-1-cyclopropyl]-2-(1,2,4-triazol-1-yl)-ethan-1-ol, or 1-phenyl-1-[1-(1,2,4-triazol-1-yl)-1-cyclopropyl]-2-(1,2,4-triazol-1-yl)-ethan-1-ol, or an addition product thereof with an acid or metal salt.

11. A method of combating fungi which comprises applying to such fungi or to a fungus habitat a fungicidally effective amount of a compound or addition product according to claim 1.

12. The method according to claim 11, wherein such compound is 1-(4-chlorophenyl)-1-[1-(1,2,4-triazol-1-yl)-1-cyclopropyl]-2-(1,2,4-triazol-1-yl)-ethan-1-ol, 1-(4-fluorophenyl)-1-[1-(1,2,4-triazol-1-yl)-1-cyclopropyl]-2-(1,2,4-triazol-1-yl)-ethan-1-ol, 1-(4-biphenyl)-1-[1-(1,2,4-triazol-1-yl)-1-cyclo-propyl]-2-(1,2,4-triazol-1-yl)-ethan-1-ol, 1-(4-methylphenyl)-1-[1-(1,2,4-triazol-1-yl)-1-cyclopropyl]-2-(1,2,4-triazol-1-yl)-ethanol-1-ol, or 1-phenyl-1-[1-(1,2,4-triazol-1-yl)-1-cyclopropyl]-2-(1,2,4-triazol-1-yl)-ethan-1-ol, or an addition product thereof with an acid or metal salt.

13. A compound of the formula

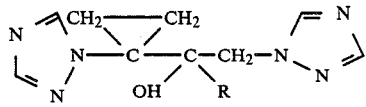

and a pharmaceutically or agriculturally acceptable salt thereof, wherein R is selected from the group consisting of chlorophenyl, fluorophenyl, dichlorophenyl, difluorophenyl and 5-chloropyrid-2-yl.

* * * * *

UNITED STATES PATENT AND TRADEMARK OFFICE
CERTIFICATE OF CORRECTION

PATENT NO. : 4,875,928

DATED : October 24, 1989

INVENTOR(S) : Regel et al.

It is certified that error appears in the above-identified patent and that said Letters Patent is hereby corrected as shown below:

Col. 27, claim 1, line 7    Delete " alkvinyl " and substitute --alkynyl--.

Col. 30, claim 12, line 2    Delete " -ethanol " and substitute -- -ethan --

Signed and Sealed this

Third Day of September, 1991

*Attest:*

HARRY F. MANBECK, JR.

*Attesting Officer*    *Commissioner of Patents and Trademarks*